United States Patent [19]

Uekusa

[11] Patent Number: 5,039,225

[45] Date of Patent: Aug. 13, 1991

[54] APPARATUS FOR MEASUREMENT OF REFLECTION DENSITY

[75] Inventor: Tadashi Uekusa, Kanagawa, Japan

[73] Assignee: Fuji Photo Film Co., Ltd., Kanagawa, Japan

[21] Appl. No.: 331,121

[22] Filed: Mar. 31, 1989

[30] Foreign Application Priority Data

Apr. 1, 1988 [JP] Japan .................................. 63-80396

[51] Int. Cl.$^5$ ............................................ G01N 21/55
[52] U.S. Cl. .................................... 356/448; 356/259; 356/446
[58] Field of Search ...................... 356/445–448, 356/352, 73.1, 432, 433, 435, 444, 244, 237, 239; 436/530; 435/12

[56] References Cited

U.S. PATENT DOCUMENTS

| | | | |
|---|---|---|---|
| 3,822,098 | 7/1974 | Rudder et al. | 356/448 |
| 4,029,419 | 6/1977 | Schumann, Jr. et al. | 356/448 |
| 4,066,403 | 1/1978 | Bruschi | 435/12 |
| 4,260,263 | 4/1981 | Kummer | 356/448 |
| 4,365,896 | 12/1982 | Mihalow | 356/446 |
| 4,629,322 | 12/1986 | Pollard | 356/446 |
| 4,753,530 | 6/1988 | Knight et al. | 356/448 |

Primary Examiner—Richard A. Rosenberger
Assistant Examiner—Hoa Pham
Attorney, Agent, or Firm—Sughrue, Mion, Zinn, Macpeak & Seas

[57] ABSTRACT

An apparatus for measurement of optical reflection density of a surface of an article, such as a color developed analytical tape for clinical test. The apparatus comprises a support for supporting the article, a source of pulsed light and two light detectors. An optical guide directs the pulsed light to the surface of the article in a direction at an angle other than 90° to the surface of the article. A light-transmissive flat plate is arranged between the optical guide and the surface of the article and may be oriented at an angle from 0° to 90° with the surface of the article to be measured. One of the light-detectors detects a portion of the pulsed light reflected from the surface of the light-transmissive flat plate as reference light, and the second light-detector detects a vertically reflected portion of the pulsed light diffusely reflected on the surface of the article. Light detected from the second detector may be provided for analysis after comparison with respect to the reference light of the first detector.

4 Claims, 4 Drawing Sheets

APPARATUS FOR MEASUREMENT OF REFLECTION DENSITY

FIELD OF THE INVENTION

The present invention relates to an apparatus for measurement of optical reflection density of a surface of an article such as a color developed-analytical tape for clinical test.

BACKGROUND OF THE INVENTION

It is important for clinical chemical texts in the present medical treatment to quantitatively determine various analytes in body fluids (whole blood, plasma, serum, urine, seliva, etc.) so as to make accurate diagnosis and proper treatment. For the purpose of performing such quantitative analysis, biochemical analytical methods using a multilayer analytical element in the form of a slide containing an analytical element or a continuous analytical element film and spectroscopic measurement have been proposed and put to practical use.

In a quantitative analysis using a multilayer analytical element, a small amount of a liquid sample to be analyzed is applied (spotted) on a multilayer analytical element and incubated at a given temperature for a given period of time to cause a color reaction between an analyte in the liquid and a reagent in the element. Then the analyte is quantitatively determined by spectroscopically measuring a reflection optical density of the color formed by the reaction.

As a light source for measuring reflection density, there is advantageously used a source which emits a pulsed light, such as a pulse xenon source, which has the advantage of generating a light usable for the analysis having a high intensity in proportion input to power and evolved heat. The pulse xenon source is particularly favorable for giving a light at a wavelength of 300-400 nm, which is important for certain analytical elements. Reflectance in the measurement of reflection density is determined as a ratio of an intensity of light reflected from a surface of an article (object) to be measured to an intensity of light generated by a light source (namely, an intensity of reference light). The intensity of a reference light is heretofore determined by irradiating separately a white board with a light generated by the same light source and measuring an intensity of light reflected therefrom. The reflection density is not always determined accurately by measuring the intensity of reference light in that way, because the intensity of light generated by the source of pulsed light varies, in a strict sense, for every pulse and the measured intensity of light does not always precisely coincide with the intensity of light which is used for the irradiation of the article. Alternatively, the reference light can be taken out of a light of the light source using an optical fiber or the like. However, thus obtained reference light is not reliably employable, because the intensity of the generated light is not always uniformly distributed around a site from which the light is generated.

Accordingly, it is desired to precisely measure the intensity of reference light every time the reflection density is determined for obtaining exact results of the analysis.

SUMMARY OF THE INVENTION

It is an object of the present invention to provide an apparatus for measurement of reflection optical density, which is particularly favorable for colorimetric analysis using a multilayer analytical element.

It is another object of the invention to provide an apparatus for measurement of reflection optical density using a source of pulsed light that is not influenced by the fluctuation of an intensity of pulsed light from the light source.

It is a further object of the invention to provide an apparatus for measurement of reflection optical density with improved accuracy and simplified procedure.

There is provided by the present invention an apparatus for measurement of optical reflection density of a surface of an article comprising:
  a support for fixing the article;
  a source of emitting a pulsed light;
  a optical means for guiding the pulsed light to the surface of the article in a direction at an angle other than 90° to the surface of the article;
  a light-transmissive flat plate arranged between the optical means and the surface of the article at an angle other than 90° to the direction of the pulsed light;
  a first light detector for detecting a portion of the pulsed light reflected from the light-transmissive flat plate as reference light; and
  a second light detector for detecting a portion of the pulsed light diffusely reflected from the surface of the article, said portion being directed vertically from the surface of the article, as a reflected light of the surface of the article.

DETAILED DESCRIPTION OF THE INVENTION

The apparatus for measurement of reflection density of the present invention will be described in detail by referring to the attached drawings.

Figure 1:
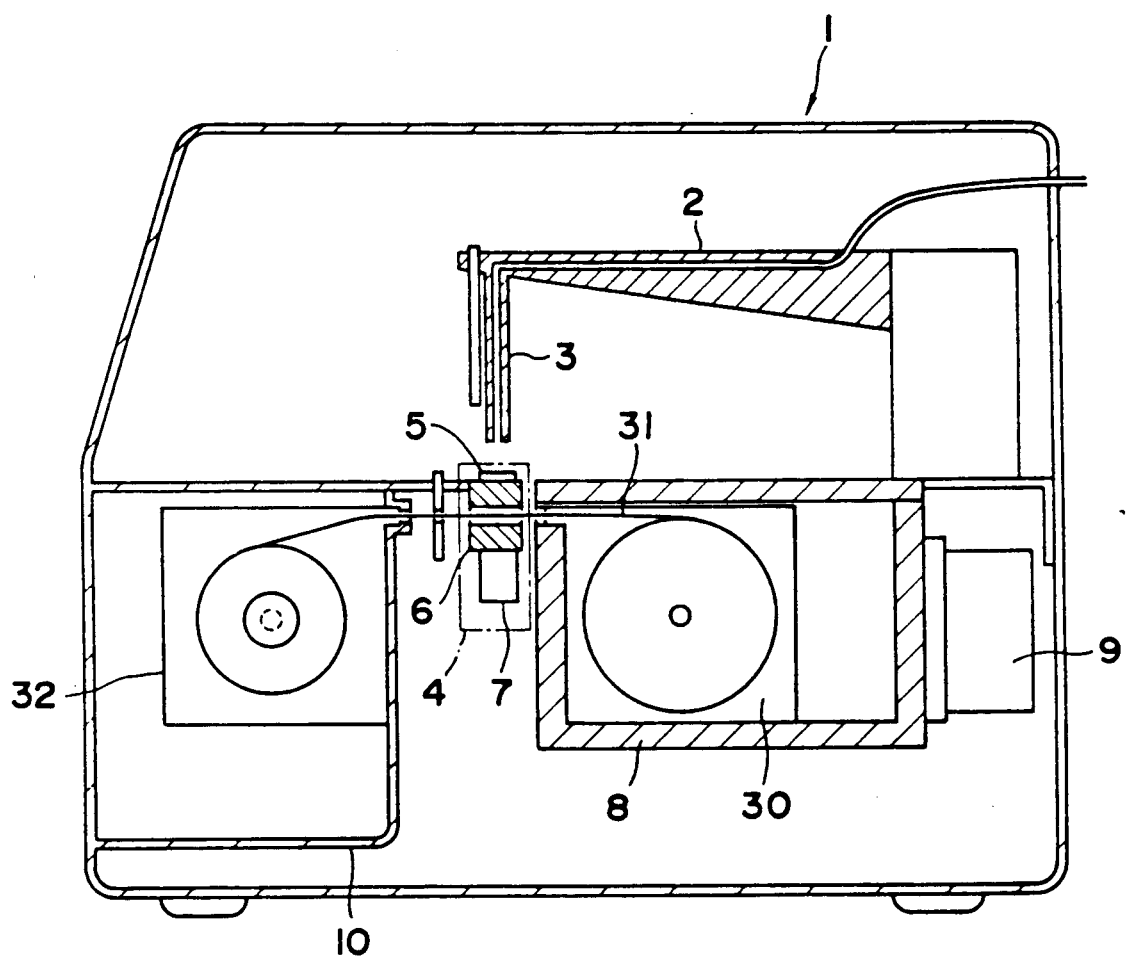
FIG. 1 is a schematic cross-sectional view of an embodiment of an apparatus for biochemical analysis which is equipped with an apparatus for measurement of reflection density according to the invention.

In the analytical apparatus of FIG. 1, at the upper area, there is provided a means 2 for spotting a liquid sample containing an analyte. A spotting nozzle 3 connected to the spotting means 2 is arranged just above an analytical section 4 which is positioned in the vicinity of center of the analytical apparatus 1. Through the analytical section 4, an analytical tape 31 is moved. The spotting means 2 is movable laterally on the plane vertical to the direction of movement of an analytical tape. The analytical section 4 is equipped with a shutter 5, an incubator 6 and an apparatus of the invention for measurement of reflection density 7. If desired, plural analytical sections may be aligned laterally on the plane vertical to the direction of movement of the analytical tape. The analytical section 4 can be moved laterally on the above plane in association with movement of the spotting means 2. In the lower half part of the analytical apparatus 1, there is provided a cold insulation container (namely, cooling container) 8 having a cassette 30 which is charged with an unused portion of an analytical tape 31 for biochemistry. The cooling container 8 can be charged with plural cassettes which may be arranged in line. The cooling container 8 can be adjusted to have a desired low temperature and low humidity by a dehumidifying cooler 9. On the side opposite to the cooling container 8, there is provided a wind-up chamber 10 which contains a cassette 32 for receiving a used portion of the analytical tape. The analytical section 4 is positioned between the two cassettes.

In performing analysis of a liquid sample using an analytical tape for colorimetry and the apparatus 1 for biochemical analysis, an unused portion of the analytical tape 31 drawn out of the cassette 30 is moved to the analytical section 4; a liquid sample is spotted (deposited) through the spotting nozzle 3 on the analytical tape 31; the incubator 6 is closed by means of the shutter 5 to be kept at a given temperature (for example, 37° C.); and incubation is carried out for a certain period of time. In the course of or after the incubation, a reflection optical density of the analytical tape 31 at the sample-spotted area is measured by the measuring apparatus 7.

Figure 2:
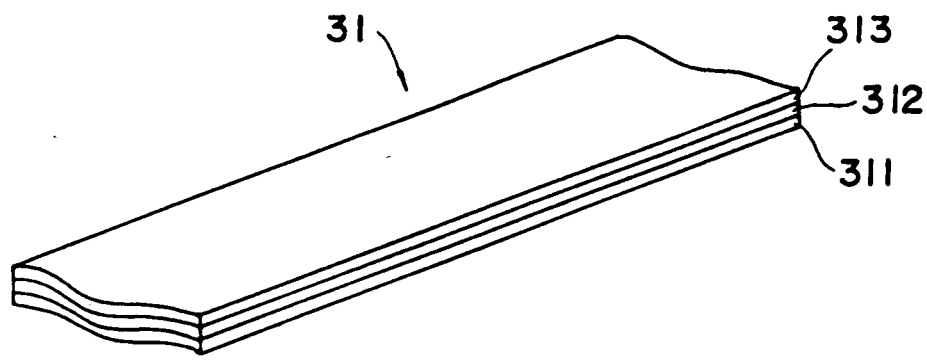
FIG. 2 is a perspective view of an analytical tape to be measured colorimetically in the apparatus of the invention.

An example of the analytical tape 31 in the form of a multilayer analytical element is illustrated in FIG. 2. In FIG. 2, the analytical tape 31 for colorimetry comprises a light-transmissive support 311, a reagent layer 312 and a spreading layer 313, laminated in order. In the colorimetric analysis, when a liquid sample is spotted on the spreading layer 313, the sample spreads in the spreading layer 313 and a substance to be analyzed (i.e., analyte) reaches the reagent layer 312 where the analyte reacts with a reagent contained therein to form a color. Optical density of the formed color is measured from the side of the support 311 by reflection photometry to analyze the analyte in the liquid sample based on the principle of colorimetry. The colorimetric analytical tape 31 may contain other known layers such as a light-reflecting layer, a light-blocking layer, a filtering layer, a registration layer, a water-absorbing layer and an undercoating layer. If desired, the spreading layer and the reagent layer may be combined to form a single layer. The structure of the analytical tape 31 is known and the article to be measured by using the apparatus of the invention may have any desired structure.

Figure 3:
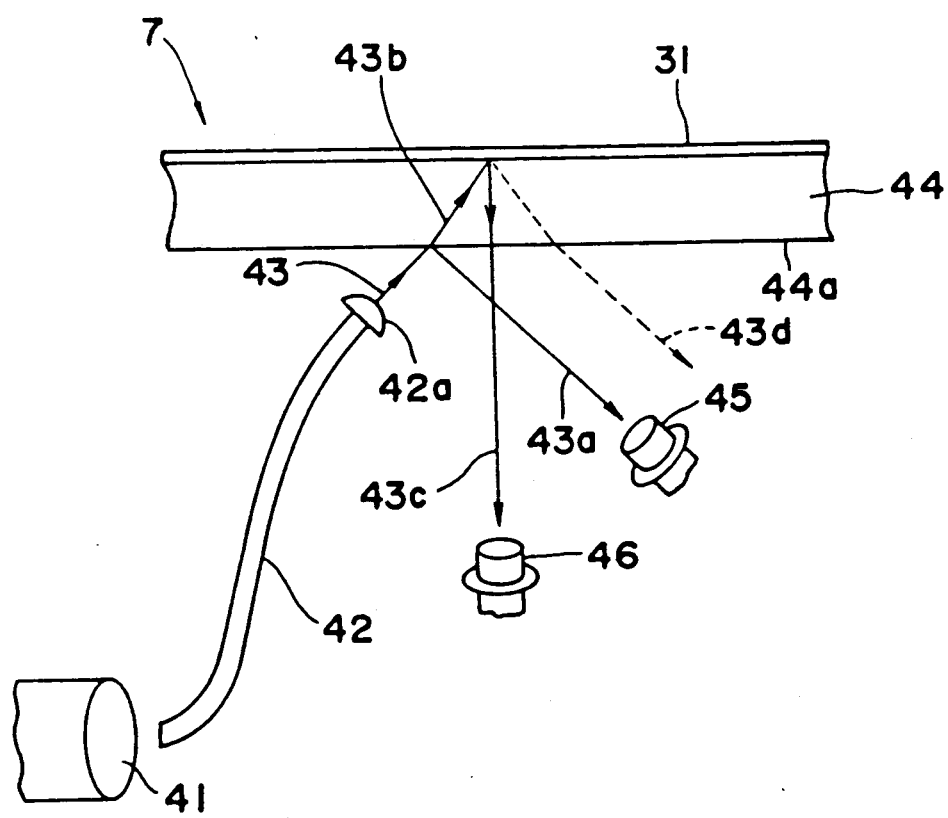
FIGS. 3, 4, 5 and 6 are schematic views of various embodiments of principal parts of the apparatus of the invention.

In FIG. 3, the apparatus 7 for measurement of reflection density is provided with a pulsed light source (i.e., a source of pulsed light) 41, a light guiding means 42, a light-transmissive flat plate 44, a first light-receiving device (i.e., light detector) 45 for detecting reference light and a second light-detector 46 for detecting light reflected on the analytical tape 31. The light guiding means 42 is arranged in such a manner that pulsed light 43 is guided to a surface 44a of the light-transmissive plate 44 and impinged upon the plate surface 44a at an angle other than 90° (i.e., at a non-perpendicular angle). At the end of the light guiding means 42, a plastic lens 42a is so provided that the pulsed light 43 converges to be focused on the surface of the analytical tape. On the other surface of the light-transmissive plate 44, a light-transmissive support 311 (FIG. 2) of the analytical tape 31 which is an article to be measured is set in contact therewith. The pulsed light 43 is impinged upon the surface of the analytical tape 31 at an angle other than 90° (i.e., at a non-perpendicular angle).

The light-detector 45 for reference light is set in such a position as to receive and detect the reflected light 43a as reference light, which is a part of the pulsed light 43 and regularly reflected on the surface 44a of the light-transmissive plate 44. The remaining portion 43b of the pulsed light 43 passes through the light-transmissive plate 44 and reaches a colored part (e.g., reagent layer 312) of the analytical tape 31, where a part of the light 43b is absorbed and the remaining portion is diffusely reflected. The light-detector 46 for reflected light is placed in such a position as to receive and detect reflected light 43c as light reflected on the surface of the article to be measured, which is a part of the diffusely reflected light and reflected in the direction vertical to the surface of the analytical tape 31.

Since the apparatus 7 for measurement of reflection density is constructed as described above, the path of light 43d regularly reflected from the interface between the light transmission plate and the analytical tape 31 is positioned apart from and parallel to the light path of the reflected light 43a entering the light-detector 45 for reference light owing to the existence of the light-transmissive plate 44 as shown in FIG. 3. Therefore the reflected light 43d does not enter the light-detector 45 for reference light. As a result, the intensity of the pulsed light 43 is accurately measured using the light-detector 45 for reference light without being influenced by the condition of the analytical tape 31. There is obtained the reference light exactly corresponding to the light reflected on the surface of the article to be measured (analytical tape 31) if the intensity of light generated by the light source 41 fluctuates for every pulse, because the reflected light 43a of reference light is just a part of the pulsed light 43 which is impinged on the surface of the article.

The intensity of the reference light received by the light-detector 45 and the intensity of the reflected light from the article received by the light-detector 46 are converted to appropriate signals, which are sent to a computer (not shown) and subjected to processing, so that the reflection density of the surface of the article to be measured is accurately determined.

The source of pulsed light 41 can be selected from various light sources. An example of the light source is a known xenon flash lamp (xenon arc lamp).

Examples of the material of the light guiding means 42 include light-guiding materials capable of guiding light effectively such as quartz fiber, glass fiber and plastic fiber. In place of providing the light guiding means 42, it is possible to have the generated pulsed light to pass through an appropriate lens system and to reach the surface 44a of the light-transmissive flat plate 44. A single or plural light guiding means may be employed for one light source 41.

There may be provided suitable optical convergent means such as a group of lens and/or suitable filters in correspondence with the desired wavelength of light employed in the measurement on the path of the pulsed light 43 from the light source 41 to the light-transmissive plate 44 and/or on the path of the reflected light 43a and/or on the path of the reflected light 43c. The optical convergent means and the filter may be a single element that provides both functions.

Examples of the material of the light-transmissive flat plate include a variety of inorganic glasses, organic glasses such as thermoplastic resins and thermosetting resins having a high transmission for light and combinations thereof. Especially, preferred is a material that reflects the pulsed light at a reflectance of 4-15% at the surface of the light-transmissive plate. The thickness of the light-transmissive plate is usually in the range of 1-10 mm.

The light-detector 45 for reference light and the light-detector 46 for reflected light are respectively selected from any conventional light-detectors such as a photodiode.

The angle of the pulsed light 43 impinged on the light-transmissive flat plate 44 (namely, incident angle) is not limited, so long as the light 43 is incident upon the surface 44a of the plate at a non perpendicular angle.

Figure 4:
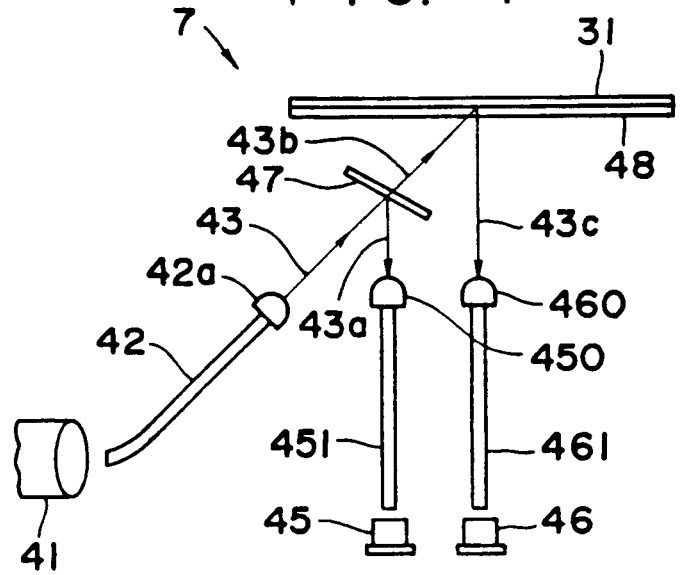
Figure 5:
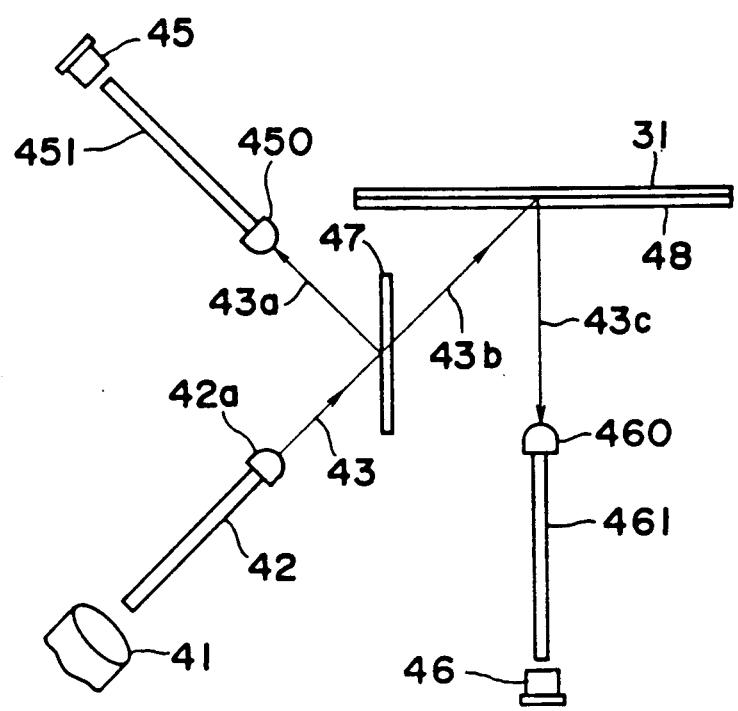
Figure 6:
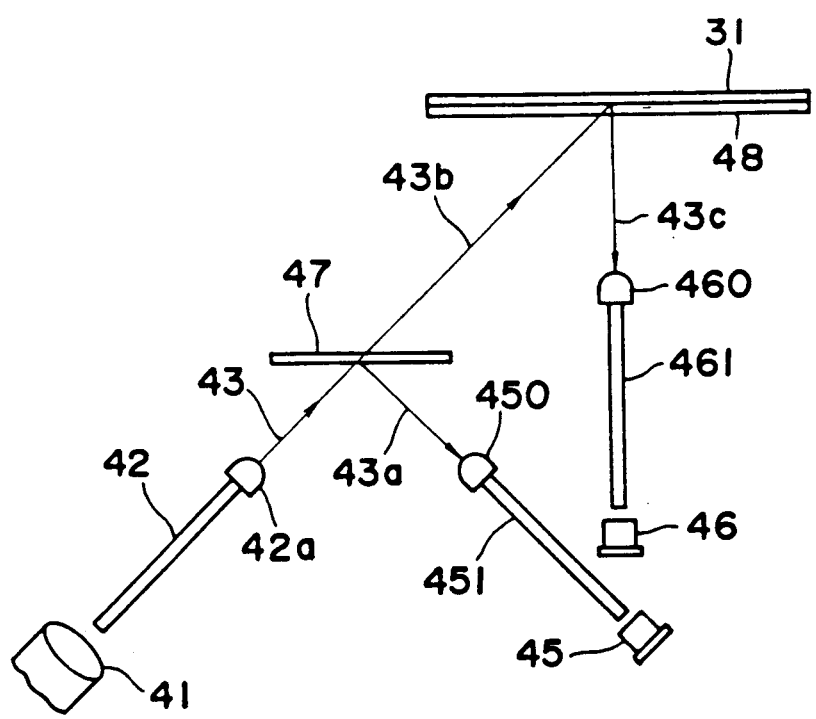

FIGS. 4 to 6 are schematic views of various embodiments of principal parts of the apparatus for measurement of reflection density.

In FIG. 4, the apparatus 7 for measurement of reflection density comprises a source of pulsed light 41, a light guiding means 42, a light-transmissive flat plate 47, a light-detector 45 for reference light and a light-detector 46 for reflected light. The light guiding means 42 is arranged in such a way that pulsed light 43 generated by the light source 41 is directed onto a surface of the light-transmissive plate 47 and impinged upon the surface of the plate 47 at an angle other than 90°. At the end of the light guiding means 42, a plastic lens 42a is so provided that the pulsed light 43 converges and is focused on a surface of an article to be measured. An analytical tape 31 to be measured is set on a thin glass plate 48 in such a manner that a light-transmissive support 311 of the tape is in contact with the glass plate 48. The light-transmissive plate 47 can be arranged at any angle from 0° to 90° (both exclusive) with the surface of the article to be measured. The pulsed light 43b having passed through the light-transmissive plate 47 is to be impinged on the analytical tape 31 at an angle other than 90°.

In a position where reflected light 43a, being a part of the pulsed light 43 and regularly reflected by the surface of the light-transmissive flat plate 47, is received and detected as reference light, a plastic lens 450 for collecting the reflected light 43a is provided. To the plastic lens 450 is connected an end of a light guiding means 451 for guiding the reflected light 43a to the light-detector 45 for reference light. At the other end of the light guiding means 451, the light-detector 45 for reference light is set. The remaining portion 43b of the pulsed light 43 passes through the light-transmissive plate 47 and reaches a colored portion (e.g., reagent layer 312) of an analytical tape 31, where a part of the light is absorbed and the remaining portion is diffusely reflected. In a position where reflected light 43c, being a part of the diffusely reflected light and reflected in the direction vertical to the surface of the analytical tape 31, is received and detected as light reflected on the surface of the article, a plastic lens 460 for collecting the reflected light 43c is provided. To the plastic lens 460, an end of a light guiding means 461 for guiding the reflected light 43c to the light-detector 46 for reflected light is connected. At the other end of the light guiding means 461, the light-detector 46 for reflected light is arranged.

Since the apparatus 7 for measurement of reflection density is constituted as described above, the intensity of the pulsed light 43 is accurately measured using the light-detection device 45 for reference light without being influenced by the condition of the analytical tape 31. There is obtained the reference light which is not affected by the fluctuation of the intensity of light generated by the source of pulsed light 41 and is exactly corresponding to the light reflected on the surface of the article to be measured (analytical tape 31), because the reflected reference light 43a is just a part of the pulsed light 43 which is impinged upon the surface of the article.

For the embodiment of FIG. 4, the source of pulsed light 41, the light guiding means 42 (it can be replaced with a lens system), the light-detector 45 for reference light and the light-detector 46 for reflected light are respectively the same as those described referring to FIG. 3. The light-transmissive flat plate 47 is the same as the light-transmissive flat plate 44 shown in FIG. 3.

In FIG. 5, the apparatus 7 for measurement of reflection density is constructed in the same manner and makes the same function as those of FIG. 4 except that a light-transmissive flat plate 47 is arranged vertical to the plane of an analytical tape 31 (corresponding to said arrangement, the direction of reflected light 43a is changed and the setting position of a light-detector 45 for reference light is different).

In FIG. 6, the apparatus 7 for measurement of reflection density is constructed in the same manner and makes the same function as those of FIG. 4 except that a light-transmissive flat plate 47 is arranged parallel to the plane of an analytical tape 31 (corresponding to said arrangement, the direction of reflected light 43a is changed and the setting position of a light-detector 45 for reference light is different).

In the description hereinbefore, it is described to refer to the apparatus for measurement of reflection density provided as a part of an apparatus for biochemical analysis therein. It should be understood that the use of the apparatus of the invention is by no means restricted to said purpose and the apparatus is applicable to various use of measuring reflection density.

I claim:

1. An apparatus for measurement of optical reflection density of a clinical analytical tape comprising:
    a flash lamp which emits a pulsed light;
    a light-transmissive flat support for supporting the tape on one surface thereof, said support having a reflectance which permits reflection of 4–15% of said pulsed light;
    light-guiding means for guiding said pulsed light to a surface of the tape in a direction at an angle other than 90° to the surface of the tape;
    a first light-detector for detecting reference light, which is a portion of said pulsed light reflected from the light-transmissive flat support; and
    a second light-detector for detecting a portion of said pulsed light diffusely reflected from the tape, said portion being directed perpendicular to the surface of the tape.

2. The apparatus as claimed in claim 1, wherein said light-guiding means has at its end a lens for converging said pulsed light to be focused on the surface of the tape.

3. The apparatus as claimed in claim 1, wherein the flash lamp is a xenon flash lamp.

4. The apparatus as claimed in claim 1, wherein said light-guiding means is a quartz fiber, glass fiber or plastic fiber.

* * * * *